(12) United States Patent
Kipperman

(10) Patent No.: US 7,824,438 B2
(45) Date of Patent: Nov. 2, 2010

(54) METHOD FOR PLACEMENT OF A STENT ASSEMBLY IN A BIFURCATED VESSEL

(76) Inventor: Robert Kipperman, 6 School Ave., Chatham, NJ (US) 07928-1657

( * ) Notice: Subject to any disclaimer, the term of this patent is extended or adjusted under 35 U.S.C. 154(b) by 1032 days.

(21) Appl. No.: 11/428,934

(22) Filed: Jul. 6, 2006

(65) Prior Publication Data
US 2008/0009937 A1 Jan. 10, 2008

(51) Int. Cl.
A61F 2/06 (2006.01)

(52) U.S. Cl. ...................... 623/1.11; 623/1.35

(58) Field of Classification Search ............... 623/1.11, 623/1.35
See application file for complete search history.

(56) References Cited

U.S. PATENT DOCUMENTS

| | | | |
|---|---|---|---|
| 4,739,762 | A | 4/1988 | Palmaz |
| 5,759,191 | A | 6/1998 | Barbere |
| 5,895,406 | A | 4/1999 | Gray et al. |
| 5,922,021 | A | 7/1999 | Jang |
| 6,086,611 | A | 7/2000 | Duffy et al. |
| 6,120,536 | A | 9/2000 | Ding et al. |
| 6,179,856 | B1 | 1/2001 | Barbere |
| 6,254,593 | B1 * | 7/2001 | Wilson ............... 623/1.11 |
| 6,379,383 | B1 | 4/2002 | Palmaz et al. |
| 6,440,165 | B1 | 8/2002 | Richter et al. |
| 6,520,988 | B1 | 2/2003 | Colombo et al. |
| 6,923,829 | B2 | 8/2005 | Boyle et al. |
| 6,936,066 | B2 | 8/2005 | Palmaz et al. |
| 6,962,202 | B2 | 11/2005 | Bell et al. |
| 6,962,602 | B2 | 11/2005 | Vardi et al. |
| 7,037,332 | B2 | 5/2006 | Kutryk et al. |
| 2001/0016768 | A1 * | 8/2001 | Wilson et al. .............. 623/1.11 |
| 2004/0172121 | A1 * | 9/2004 | Eidenschink et al. ....... 623/1.11 |
| 2004/0186560 | A1 | 9/2004 | Alt |
| 2005/0131530 | A1 | 6/2005 | Darack |

OTHER PUBLICATIONS

Marco A. Costa et al., "Molecular Basis of Restenosis and Drug-Eluting Stents," Circulation—Journal of the American Heart Association, cover page & pp. 2257-2273 (May 3, 2005) (downloaded from circ.ahajournals.org).

* cited by examiner

Primary Examiner—Anhtuan T Nguyen
Assistant Examiner—Tin Nguyen
(74) Attorney, Agent, or Firm—Panitch Schwarze Belisario & Nadel LLP

(57) ABSTRACT

A method for placing a stent assembly in a bifurcated vessel in an animal body, such as a human, includes inserting primary and secondary guidewires from a location external of the body through the primary vessel. The second guidewire is also inserted into the secondary or branch vessel beyond a bifurcation area. The primary and secondary guidewires are then inserted into a primary stent and catheter assembly such that the assembly can move along the guidewires into and through the primary vessel to the bifurcation area where the primary stent is expanded. While retaining the secondary guidewire in the vessels, the remainder of the catheter assembly and primary guidewire are removed. Then the secondary stent, mounted on a catheter, is passed through the primary vessel using the secondary guidewire as a guide, past the bifurcation area and into the secondary vessel. There, the secondary stent is expanded to form the bifurcated stent assembly in an efficient and practical manner.

17 Claims, 3 Drawing Sheets

METHOD FOR PLACEMENT OF A STENT ASSEMBLY IN A BIFURCATED VESSEL

BACKGROUND OF THE INVENTION

The present invention relates to a method of placing a stent assembly in a bifurcated vessel. More particularly, the method includes placing a primary stent in a primary vessel and a secondary stent in at least one secondary vessel which branches from the primary vessel, the secondary branch vessel(s) and the primary vessel forming a bifurcated vessel.

A stent, sometimes referred to as a graft, is an endoprosthetic device that is placed within or implanted in a tubular vessel, such as a vascular vessel like an artery or vein, or other vessel, such as intestine, esophagus or other tubular body organ in animals, and particularly humans, for treating blockages, stenoses or aneurysms of the vessel. The stent is implanted within the vessels to act as an internal scaffold or reinforcement to support collapsing, previously fully or partially occluded, weakened or abnormally dilated portions of the vessel wall. Typically, stents have been used to treat dissections in blood vessel walls following balloon angioplasty of the coronary arteries and peripheral arteries, and to improve results of angioplasty by reinforcing the vessel wall. Stents also have been implanted in other body vessels, such as the gastrointestinal tract, particularly the urinary tract, the bile duct, the esophagus and the tracheo-bronchial tree to support weakened or otherwise damaged walls of those organs.

Typically, stents are elongated tubular products that have a first, unexpanded condition in which they are threaded through the appropriate body organs, such as blood vessels, by use of catheters and guidewires. Some stents are expanded by way of the use of a small balloon which is expandable by a fluid, such as a sterile saline solution, when the stent reaches the desired location. There are great number of examples of stents having various types of geometry, such as those disclosed in U.S. Pat. No. 4,739,762 of Palmaz (commercialized in various forms as the Palmaz stent), U.S. Pat. No. 5,895,406 of Gray et al. and U.S. Pat. No. 5,922,021 of Jang. Other types of stents have been developed that are made of materials, such as an alloy of nickel and titanium called nitinol, which, when initially compressed, are within the sheath of a catheter, are in an unexpanded state, but when released from the catheter sheath, self-expand to an appropriate degree without the use of a balloon to bear against the vessel walls and retain them in an open condition. A couple of examples of stents of this type are shown in U.S. Pat. No. 6,923,829 of Boyle et al. and U.S. Pat. No. 6,936,066 of Palmaz et al. Stents have been commercialized by Cordis Corp. (a Johnson & Johnson Company), Guidant Corp., Boston Scientific Corp., Medtronic Inc., all of the United States, and Medinol, Ltd. of Israel, among others. The manufacture and installation of stents is a multi-billion dollar business which is increasing annually, particularly as populations age.

Some stents are drug-eluting stents by virtue of the material from which the stents are made having properties particularly relating to antithrombotic activity, or antirestinosis activity. Often during procedures relating to vessel repair or even the insertion of the stents, blood may form clots, resulting in potentially serious or fatal thromboses and, over time, scar tissue or other matter builds up in the vessels, often in the vicinity of and on, and even as a result of, the use of a stent, resulting in re-blockage or restinosis of the vessel. Drug-eluting stents, which may also include coatings, thin reservoirs containing leachable active ingredients, and other techniques, have been developed and are in use to help prevent or treat such thromboses or restinosis. Among a great many examples are drug-eluting stents of a type disclosed in U.S. Pat. No. 6,120,536 of Ding et al., or U.S. Pat. No. 7,037,332 of Kutryk et al., which discloses a device coated with an antibiotic that promotes adherence of endothelial cells to the device. Certain materials used in making stents are themselves antirestentotic or antithrombogenic, such as U.S. Pat. No. 6,379,383 of Palmaz et al.

The use of stents in relatively straight and unbranched vessels is fairly straightforward. Complications arise when the damage to be repaired is near or at a junction or point of bifurcation in bifurcated vessels where a branch vessel joins a main vessel. There are difficulties in inserting stents both in the main or primary vessel and in the branched or secondary vessel, which may result in further damage to the vessel with increased risk of thrombosis and embolism or even additional perforation of the vessel. Complications that may arise are disclosed in U.S. Pat. No. 6,962,202 of Vardi et al., which discloses one type of apparatus and a method of using it for treating bifurcated vessels. Other examples of stents and methods of inserting them for use in bifurcated vessels are disclosed in U.S. Pat. No. 6,440,165 of Richter et al. and in U.S. Patent Application Publication No. US 2004/0186560, published Sep. 23, 2004. The disclosures of these and all other patents and publications mentioned herein are hereby incorporated herein by reference. Each of the patents or publication mentioned in this paragraph discloses alternative arrangements and methods of insertion. Despite the various techniques, there are still certain inefficiencies and concerns with the methods of inserting stent assemblies in bifurcated vessels. The present invention overcomes the difficulties in alignment and insertion of various types of stents.

The present invention provides a method for positively and efficiently aligning and inserting a stent assembly comprising a primary stent and a secondary stent into a bifurcated vessel. The stent may be a balloon-expandable stent or a self-expandable stent and may include a coating or be made of materials by which it may also be a drug-eluting stent. The stent is made of materials or includes imageable coatings or other markings to allow ready determination of its location within and passage through a vessel, which is particularly important when dealing with bifurcated vessels. Such coatings and technologies are well known to those skilled in the art. Substantially any type or configuration of stent may be used with the method of the present invention. The present invention provides for an improved method for placing a stent assembly and a catheter assembly for inserting the stent assembly into a bifurcated vessel, with complete stent support for the full bifurcated vessel, which reduces the risk of restenosis or other adverse consequences associated with treating bifurcated vessels.

BRIEF SUMMARY OF THE INVENTION

The present invention relates to a method for placing a stent assembly in a bifurcated vessel in an animal body, the method comprising (a) locating and assessing an area in the body for placement of a stent assembly in a primary vessel and a secondary vessel at a location where the primary vessel and the secondary vessel intersect at a bifurcation area; (b) inserting a primary guidewire from a location external of the body through the primary vessel beyond the bifurcation area; (c) inserting a secondary guidewire from a location external of the body through the primary vessel and into the secondary vessel; (d) selecting a primary stent having a lumen, a side opening, a proximal end region and a distal end region, the primary stent being configured to fit within the primary vessel in the bifurcation area, and when expanded, to maintain patency of the primary vessel where the primary stent is installed; (e) mounting the primary stent on a primary stent catheter having a lumen and a side opening such that the primary stent is expandable when in position in the bifurcation area and the side opening of the primary stent is aligned with the side opening of the primary stent catheter; (f) inserting the primary guidewire through the lumen of the primary stent catheter surrounded by the distal end portion of the primary stent and extending through the lumen of the primary stent catheter surrounded by the proximal end region of the primary stent; (g) inserting the secondary guidewire into the aligned side openings of the primary stent and the primary stent catheter and extending through the lumen of the primary stent catheter surrounded by the proximal end region of the primary stent; (h) passing the primary stent catheter through the primary vessel and into the bifurcated area for placement of the primary stent within the primary vessel; (i) expanding the primary stent to maintain patency of the primary vessel in and adjacent to the bifurcation area, such that the side opening in the primary stent is aligned with the secondary vessel; (j) withdrawing the primary stent catheter and the primary guidewire from the primary vessel, while retaining the secondary guidewire in the primary and secondary vessels; (k) selecting a secondary stent having a lumen, a proximal end region and a distal end region, the secondary stent being configured to fit within the secondary vessel in the bifurcation area, and when expanded, to maintain patency of the secondary vessel where the secondary stent is installed; (l) mounting the secondary stent on a secondary stent catheter having a lumen such that the secondary stent is expandable when in position through the side opening of the primary stent in the bifurcation area and when in position in the secondary vessel; (m) inserting the secondary guidewire into the secondary stent catheter lumen beginning from a portion surrounded by the distal end region of the secondary stent and extending through the lumen of the secondary stent catheter surrounded by the proximal end region of the secondary stent; (n) passing the secondary stent catheter through the primary vessel, through the proximal end region and side opening of the expanded primary stent into the bifurcated area for placement of the secondary stent within the secondary vessel and in fluid communication with the expanded primary stent; (o) expanding the secondary stent to maintain patency of the secondary vessel such that the proximal end region of the secondary stent is in fluid communication and in contact with the side opening of the expanded primary stent; and (p) withdrawing the secondary stent catheter and the secondary guidewire from the secondary and primary vessels to a location external of the body.

As used herein, the article "a," "an" or a singular component includes the plural or more than one component, unless specifically and explicitly restricted to the singular or a singular component. Thus, for example, reference to "a secondary vessel" means one or more than one secondary vessel that may be associated with a primary vessel as part of a bifurcated vessel.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
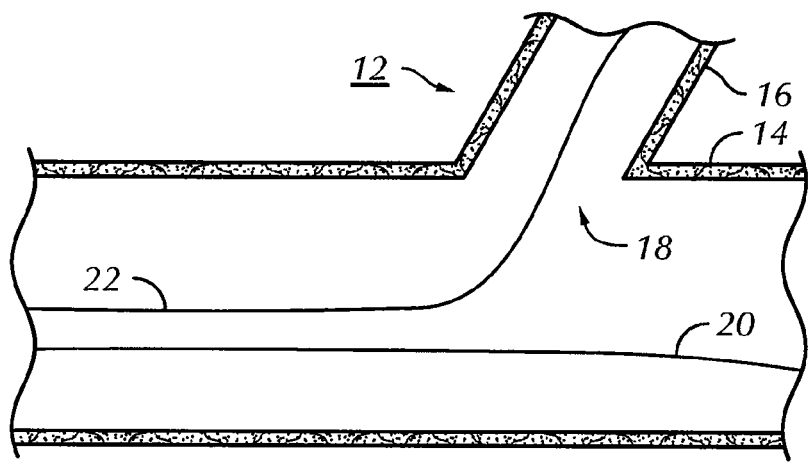
FIG. 1 is a schematic representation of a bifurcated vessel showing the insertion of primary and secondary guidewires therein as initial steps in the method of the present invention prior to the placement of the stent assembly in the desired location within a bifurcated vessel.

The present invention relates to various embodiments of methods for placing a stent assembly in a bifurcated vessel in an animal body, preferably a human, where the vessels may be any type of bifurcated vessel as mentioned above, but particularly vascular vessels. Coronary vessels such as the aorta and its branches, renal arteries, great arch vessels such as subclavian, carotid and brachiocephalic vessels, are particularly preferred. Also, although the schematic depictions and descriptions herein relate to the insertion of a secondary stent into a single secondary vessel branching from a primary vessel, the same method may be applied to two or more branches extending from a primary vessel.

As mentioned above, any type of stent may be used, including stents of various geometry made of stainless steel, titanium, nitinol, nickel-chromium alloys, cellulose, and various synthetic polymeric plastics. Moreover, the primary and secondary stents used in the present method may be of any desired or appropriate dimension in view of the vessels in which they are to be inserted, but typically, without limitation, a primary stent has an expanded length of about 10 mm to about 40 mm, while a secondary stent typically, but without limitation, has an expanded length of about 5 mm to about 40 mm. The uses of the stents in particular vessels determine their diameter and length and the angle of the secondary stent with respect to the primary stent. For example without limitation, when the primary vessel is the aorta or a great arch vessel, the stents may have an expanded diameter of about 20 mm to about 50 mm. The branch vessels from the aorta are appropriately sized, and stents used therein may have an expanded diameter typically of about 4 mm to about 10 mm, while stents used in the secondary vessels from the great arch vessel typically may have an expanded diameter of about 8 mm to about 15 mm. Stents used in other coronary vessels typically may have an expanded diameter of about 2 mm to about 6 mm. Stents used with renal vessels typically may have an expanded diameter of about 4 mm to about 10 mm. The branched secondary vessels may intersect with a primary vessel at any angle. Such angle may vary, depending on the bifurcated vessels, such as at an angle of about 20° to about 120°, with typical angles being about 30°, about 45° and about 90°. Preferably, a number of stents and their associated catheters are prepared at different angles to be ready for insertion when appropriate.

Additionally, the stents may be coated with an antirestentotic coating or an antithrombogenic material. Typically, but again without limitation, the antirestentotic material is an antimetabolite. Exemplary antirestentotic materials include paclitaxol, seruliomous, everulimous, antisense ribonucleic acid or nitric oxide, for instance. Non-limiting examples of antithrombogenic materials include heparin, enoxaprin, low molecular weight heparin, antithrombin, tissue plasminogen activator, streptokinase, urokinase and various antithrombogenic polymers. The materials may be coated either on the primary stent, the secondary stent, or both, and may be in the form of a polymer reservoir or matrix allowing for the gradual release of the material.

Figure 4:
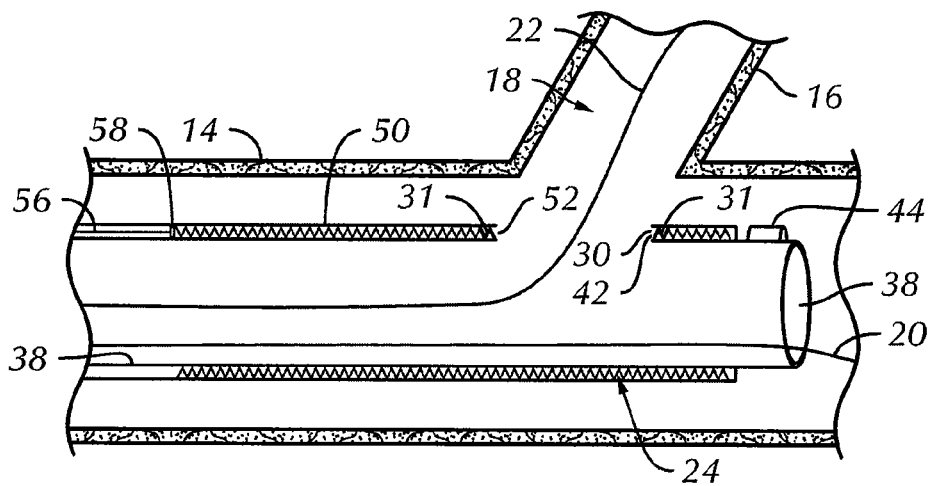
FIG. 4 schematically represents the alignment of the primary catheter, sheath and stent assembly of the first embodiment in the primary vessel such that the side openings in the primary stent catheter, the primary stent and the primary stent sheath are aligned with the opening to the secondary vessel in the bifurcation area prior to expansion of the primary stent in the primary vessel.
Figure 5:
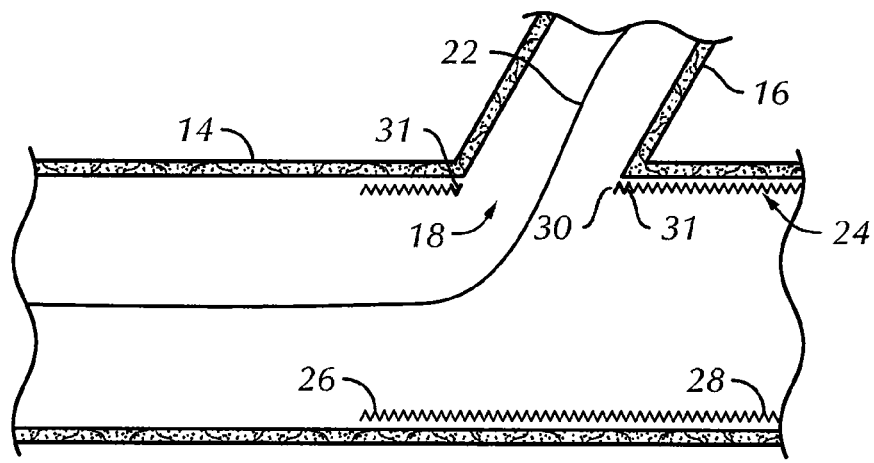
FIG. 5 schematically illustrates the placement of the primary stent within the primary vessel after the removal of the primary stent catheter assembly and the primary guidewire, while retaining the secondary guidewire in place within the secondary vessel.

As also noted above, the stents used in the method of the present invention may be self-expandable or balloon-expandable. Although FIGS. 1, 5 and 8 are generic to all types of stents, for the purposes of clarity in illustrating and explaining the method of this invention, FIGS. 2-4, 6 and 7 are directed to the use of self-expandable stents, while FIG. 9 schematically depicts the use of a balloon-expandable primary stent, where the principle would apply also to a balloon-expandable secondary stent, which is not illustrated specifically, but such stents are well known to those skilled in the art, and could be readily adapted to the present method without undue experimentation.

Figure 8:
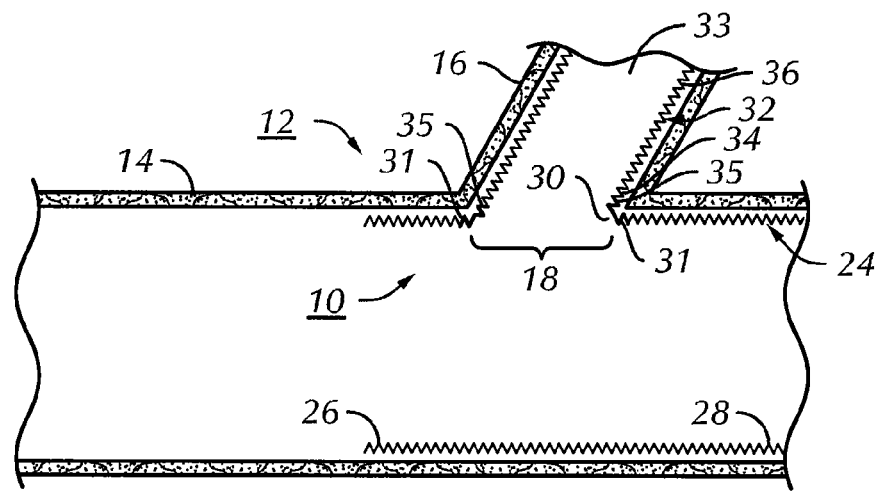
FIG. 8 schematically represents the placement of the expanded stent assembly within the bifurcated vessel after removal of the catheter assemblies and guidewires.
Figure 9:
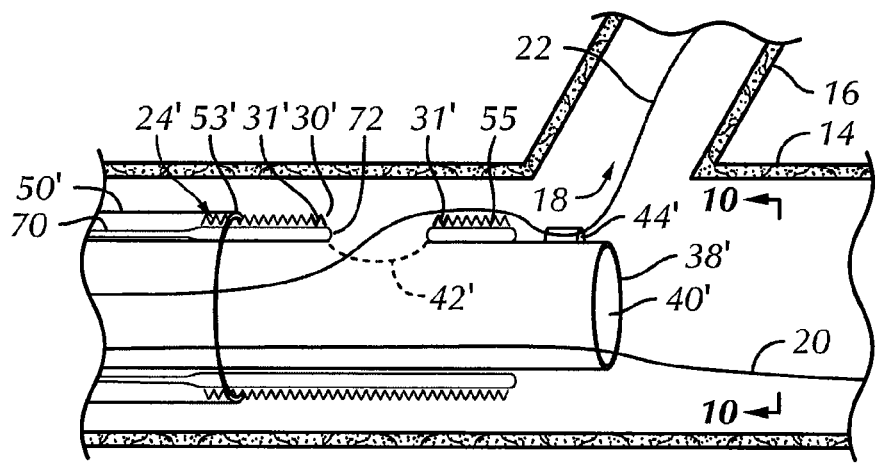
FIG. 9 is a schematic representation of an alternative embodiment of a primary stent catheter assembly for insertion of a balloon-expandable primary stent within the bifurcated vessel, prior to the expansion of the stent.

With reference to the drawings, wherein like numerals indicate like elements throughout the several views, there is shown in FIG. 8 a stent assembly 10 after insertion into a bifurcated vessel 12, which is also clearly shown in FIG. 1. The bifurcated vessel 12 includes a primary vessel 14 and at least one branch or secondary vessel 16 extending at any appropriate angle, such as about 20° to about 120°, with respect to the primary vessel 14. As noted above, for clarity and purposes of illustration, only one branch or secondary vessel 16 is illustrated, although two or more such secondary vessels, at any angles, could also be involved in the stent placement method according to the present invention. The primary vessel 14 and the secondary vessel 16 meet in a bifurcation area 18 best shown in FIGS. 1 and 8.

Figure 2:
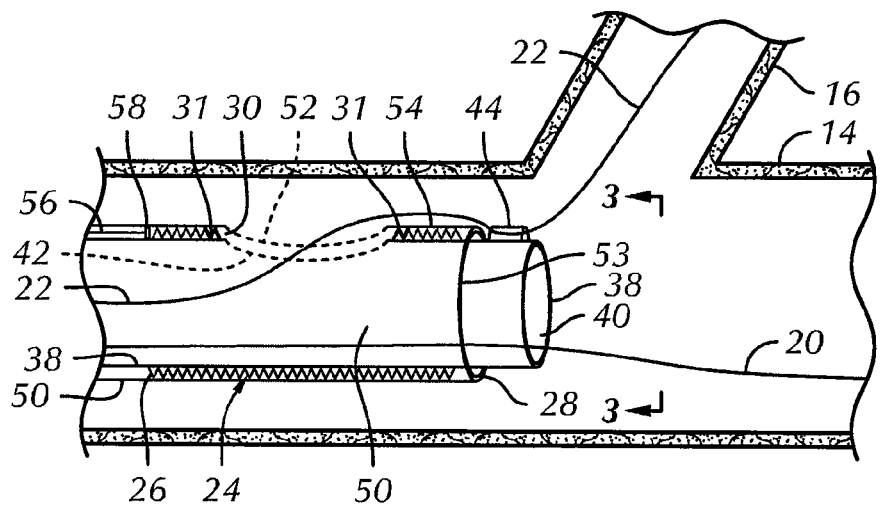
FIG. 2 is a schematic representation of a first embodiment of a primary catheter, sheath and stent assembly for inserting a self-expanding primary stent within the primary vessel in accordance with the method of the present invention.
Figure 6:
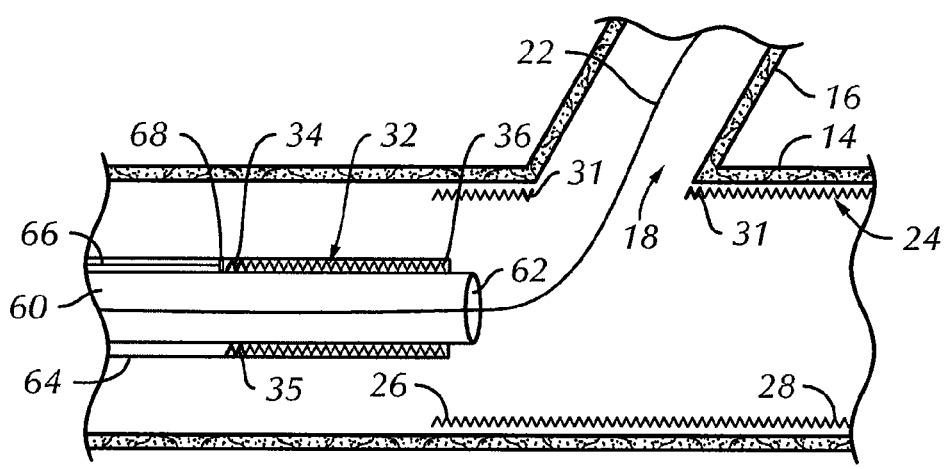
FIG. 6 schematically illustrates the insertion of an unexpanded self-expandable secondary stent on a secondary stent catheter and sheath assembly prior to insertion of the secondary stent into the secondary vessel.

Again with reference to FIG. 8, and also with reference to FIGS. 2 and 6, the stent assembly 10 includes a primary stent 24 for expansion and implantation within the primary vessel 14. The primary stent 24 includes a primary stent lumen 25, a proximal end region 26, a distal end region 28 and a side opening 30 between the proximal and distal end regions.

The stent assembly 10 also includes a secondary stent 32 having a lumen 33, a proximal end region 34 and a distal end region 36. The secondary stent 33 is implanted within the secondary vessel 16 such that its lumen 33 is in fluid communication with the lumen 25 of the primary stent 24 through the side opening 30 of the primary stent 24. Preferably, as shown in FIG. 8, the end of the secondary stent 32 in the proximal end region 34 is in contact with the wall of the primary stent 24 surrounding the side opening 30. The side opening 30 may be of any appropriate shape to correspond with the angle of the secondary stent 32 and the secondary stent 32 would have the appropriate shape to mate with the side opening 30 in the primary stent 24 to completely support the bifurcated vessels.

Although bifurcated stent assemblies are known in the art, the present invention relates to a more efficient and positive placement or insertion method with better alignment than is believed possible with prior art stent insertion methods resulting in a bifurcated stent assembly. Problems associated with such prior art insertion methods include the need to fish a secondary guidewire into the secondary lumen after the primary stent has been expanded, special shapes or angled portions of secondary stents, such as a flared proximal end portion, insertion methods which rely on the use of two balloons to expand a primary stent while aligning a primary stent opening with the lumen of the secondary vessel, and other problems, where insertion is difficult or uncertain and/or time-consuming. The more difficult and time consuming the procedure, the more the patient or other subject is at risk during and after the procedure. The insertion method of the present invention overcomes or at least reduces such problems and concerns.

With reference to FIG. 1, after an initial step of locating and assessing an area in the body for placement of a stent assembly in a primary vessel 14 and a secondary vessel 16 at a location where the primary vessel and the secondary vessel intersect at a bifurcation area 18, a primary guidewire 20 is inserted from a location external of the body through the primary vessel 14 beyond the bifurcation area 18. Typically, for certain coronary vessel angioplasty procedures and associated stent insertion procedures, insertion of the guidewires is through an incision in a femoral artery. A secondary guidewire 22 is also inserted from a location external of the body through the primary vessel 14 and into the secondary vessel 16. The insertion of the secondary guidewire 22 at the initiation of the procedure is an important aspect in assuring appropriate and accurate alignment of the secondary stent in the secondary vessel.

The remainder of the insertion method will now be described with respect to a first embodiment in which the stents are self-expandable stents inserted as schematically depicted in FIGS. 2 through 7, resulting in the placement of the stent assembly 10 as shown and previously described with respect to FIG. 8.

After insertion of the guidewires as shown in FIG. 1, an appropriate primary stent 24 is selected such that the primary stent side opening 30 is appropriate in size and location with respect to the size and shape of the secondary vessel 16 in the bifurcation area 18 as determined by prior examination using various diagnostic or even exploratory surgical techniques. The stents used in the present invention are radio opaque or preferably have radio opaque or other suitable markings, such as marking 35 at least at the proximal end region 34 of the secondary stent 32, and optionally at the distal end region 36 (not shown) and, with respect to the primary stent 24, markings 31 in areas surrounding the side opening 30, and optionally at the proximal and distal end regions 26 and 28 (not shown). The markings, such as markings 31 and 35, allow for the efficient travel and/or location of the stents in the body, and the secondary stent within the primary stent, so that they can be located and assessed by any suitable technique, such as fluoroscopy, plain radiography, arteriogram, virtual arteriogram, computerized tomography, magnetic resonance imaging, or any other appropriate technique. The primary stent 24 is also configured to fit within the primary vessel 14 in the bifurcation area 18 and, when expanded, to maintain patency of the primary vessel 24 where the primary stent is installed, as shown in FIG. 8.

The primary stent 24 is mounted on a primary stent catheter 38 having a lumen 40 and also a side opening 42 of a shape, size and location corresponding to the side opening 30 of the primary stent 24 so that the openings will be in alignment.

Figure 3:
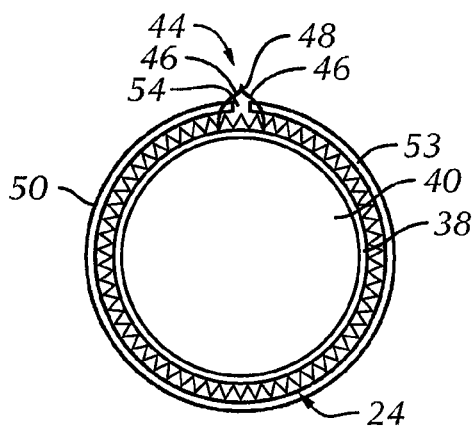
FIG. 3 depicts schematically an enlarged end elevation view of the primary catheter, sheath and stent assembly of FIG. 2 taken along lines 3-3 of FIG. 2.

As best shown in FIGS. 2 and 3, it is preferred, but not required, to use an optional peel-away wire guide 44 through which the secondary guidewire 22 is inserted, as explained below. The peel-away wire guide 44 includes side walls 46 attached to the surface of the primary catheter 38 at a location distal to the distal region 28 of the primary stent 24. The attachment may be by any sort of suitable nontoxic adhesive, melt bonding, fusion welding, etc. The peel-away wire guide 44 also includes a releasable closure member 48 of a type typically used in ZIP-LOK® reclosable plastic bags. Thus, for example, in this type of a releasable closure 48, a longitudinal male rib, with or without a small hook-like edge, is retained by friction within a longitudinal female groove with or without an interfitting hook edge reception slot for releaseably retaining the peel-away releasable closure 48 in a closed condition upon pressing the components together. The releasable closure can be opened either by manually separating the releasable member components by pulling them apart, or by any other sufficient force which overcomes the friction created by the press fit arrangement of the releasable closure. The movement of a guidewire in a direction transverse to the longitudinal closure members is sufficient to cause the friction to be overcome to release the guidewire.

Since this initial embodiment of the primary stent 24 is a self-expandable stent, to prevent the stent from expanding away from the surface of the catheter 38, a primary stent sheath 50, having a distal end 53 at the distal region 28 of the primary stent 24, as well as an opposed proximal end (not labeled) surrounds the primary stent 24. The primary stent sheath 50 also includes a side opening 52 of the same size, shape and location as the side openings 30 and 42 in the primary stent 24 and the primary stent catheter 38, respectively, all of such openings being in alignment.

The primary stent sheath 50 also includes a longitudinal groove or slot 54 in the surface of a portion of the primary stent sheath 50 between the edge of the side opening 32 and the distal end 53 of the primary stent sheath. The groove 54 is best seen in FIGS. 2 and 3. The purpose of this groove 54 is to allow the secondary guidewire 22 to pass through the groove when the sheath 50 is retracted to allow the self-expandable stent to expand.

Once the primary stent 24 is mounted on the primary stent catheter 38 and surrounded by the primary stent sheath 50, the primary guidewire 20 is inserted through the lumen 40 of the catheter 38, such that the primary guidewire 20 extends fully through the primary catheter, stent and sheath assembly. The secondary guidewire 22 is inserted at least into the aligned side openings 30, 42 and 52 of the primary stent 24, primary stent catheter 38 and primary stent sheath 50, respectively, and into the lumen 40 through the proximal end of the primary catheter, stent and sheath assembly. If the optional peel-away wire guide 44 is used, the secondary guidewire 22 is also threaded through it.

After the primary guidewire 20 and the secondary guidewire 22 are inserted into the primary stent catheter 38, the catheter and its associated primary stent 24 and primary stent sheath 50 are passed through the primary vessel 14 along the primary guidewire 20 and the secondary guidewire 22 until the assembly reaches the bifurcation area 18. At a certain point where the guidewires 20 and 22 diverge, as the primary catheter assembly is advanced along the primary guidewire 20 through the primary vessel 14, the secondary guidewire 22 will be released from the peel-away wire guide 44 if such guide is in use. The catheter assembly is then advanced to a location such that the side openings 30, 42 and 52 align with the secondary vessel 16 in the bifurcation area 18. At that time, the primary stent 24 is inserted into position within the primary vessel 14. Typically, this is accomplished by using a relatively stiff primary stent deployment wire 56 located between the primary stent catheter 38 and the primary stent sheath 50. The primary stent deployment wire 56 also has a distal primary stent deployment wire abutment member 58 which abuts the proximal end of the primary stent 24 to retain it in proper axial or longitudinal position on the catheter 38 while withdrawing the primary stent catheter sheath 50 from its retention position. When the sheath 50 is withdrawn, by which the primary stent 24 is retained on the catheter, allowing the stent 24 to expand and bear against the walls of the primary vessel 14, thus maintaining their patency. As the primary stent sheath 50 is withdrawn out of the body, or at least off of the stent 24, the secondary guidewire 22 passes through the groove 54 in the sheath 50. The position of the primary catheter, stent and sheath immediately prior to the expansion of the primary stent 24 is shown in FIG. 4. Upon retraction of the sheath and the expansion of the primary stent 24, the primary stent catheter 38, the primary stent sheath 50 and the primary guidewire 20 all may be withdrawn from the primary vessel 14. However, it is important that the secondary guidewire 22 remain in the primary vessel 14 and especially in the secondary vessel 16 as shown in FIG. 5.

Once the primary stent 24 has been inserted in the primary vessel 14 in the vicinity of the bifurcation area 18, it is time to insert the secondary stent 32 into the secondary vessel 16. This is accomplished by selecting a secondary stent 32 which is configured to fit within the secondary vessel 16 in the bifurcation area 18 and, when expanded, such stent 32 maintains the patency of the secondary vessel 16 when the secondary stent is installed. As best shown in FIG. 6, the secondary stent 32 is mounted on a secondary stent catheter 60 having a lumen 62. Since the embodiment shown in FIG. 6 is a secondary stent that is self-expandable, a secondary stent sheath 64 overlies the secondary stent 32 to keep it from expanding by itself.

The secondary guidewire 22 is then inserted into the secondary stent catheter lumen 62 beginning from a portion surround by the distal end region 36 of the secondary stent 32 and extending through the lumen 62 of the secondary stent catheter 60 through the portion surrounded by the proximal end region 34 of the secondary stent 32. Thus, the secondary stent catheter, stent and sheath assembly is threaded onto the secondary guidewire 22 and the assembly passes through the primary vessel 14 until it reaches the bifurcation area 18.

Figure 7:
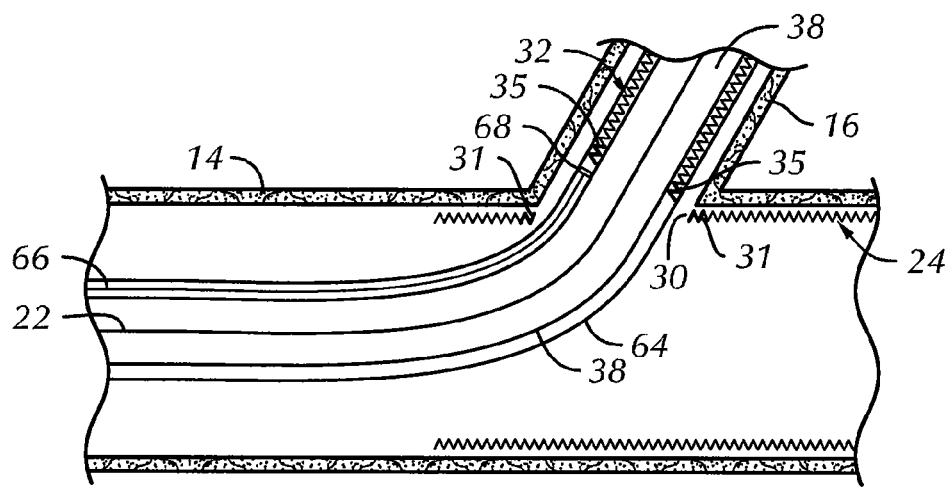
FIG. 7 schematically illustrates the insertion of the unexpanded secondary stent into the secondary vessel through the side opening in the primary stent.

Upon reaching the bifurcation area 18, as best shown in FIG. 7, the assembly travels along the guidewire 22 through the side opening 30 in the expanded primary stent 24 and into the secondary vessel 16. When the secondary stent, catheter and sheath assembly reaches the desired location within the secondary vessel 16, the secondary stent 32 is deployed by allowing it to expand. This is accomplished in a manner similar to that described above with respect to the self-expandable primary stent 24. Thus, a secondary stent deployment wire 66 having a secondary stent deployment wire abutment member 68 bears against the proximal end of the secondary stent 32, retaining it in the appropriate longitudinal position on the secondary stent catheter 38 while the secondary stent sheath 64 is withdrawn toward the body exterior, exposing the secondary stent 32 and allowing it to expand into the appropriate position as shown in FIG. 8. When properly inserted and expanded, the secondary stent 32 is in fluid communication with the expanded primary stent 24, and preferably, the proximal end of the secondary stent 32 is in contact with the wall of the primary stent 24 surrounding the side opening 30 as shown in FIG. 8.

Figure 10:
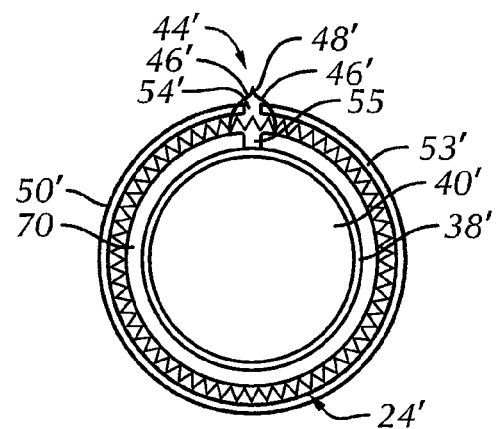
FIG. 10 depicts schematically an enlarged end elevation view of the primary catheter, sheath and stent assembly of the alternative embodiment of FIG. 9 taken along lines 10-10 of FIG. 9.

The stent assembly 10 shown in its deployed, expanded position in FIG. 8, may be deployed using balloon-expandable stents, as well as by using self-expandable stents as described above. FIGS. 9 and 10 depict a schematic representation of a primary balloon-expandable stent and catheter assembly with respect to the insertion of a balloon-expandable primary stent 24', where the primed reference numerals identify the same elements as identified by the unprimed reference numerals of the first embodiment shown in FIGS. 1-8 as described above. The method of placing a stent assembly in a bifurcated vessel using balloon-expandable stents is substantially the same as that described above with the following exceptions.

After locating and assessing an area in the body for placement of a stent assembly in a primary vessel 14 and a secondary vessel 16 where the primary and secondary vessels intersect at a bifurcation area 18, the primary guidewire 20 and the secondary guidewire 22 are inserted into the vessels as described above and shown in FIG. 1. Then the appropriate balloon-expandable primary stent 24' is selected and mounted on a balloon 70 which has a side opening 72 that is of the same shape and size and that is aligned with side opening 30' in the primary stent 24' and side opening 42' formed in the primary stent catheter 38'. The distal portion of the balloon 70 also has a groove 55 formed therein, as best seen in FIG. 10, to allow the retraction of the balloon following the expansion of the primary stent 24'. An optional sheath 50' including a groove 54', while not required where a balloon stent assembly is used, preferably is optionally used to protect the primary stent 24' and is shown as partially retracted in FIG. 9.

After the primary balloon stent and catheter assembly shown in FIG. 9 has been assembled, the primary guidewire 20 extends into the lumen 40' of the primary stent catheter 38'. The secondary guidewire 22 is inserted either directly into the lumen 40' through the side openings 30', 42' and 72 or is threaded through the optional peel-away wire guide 44', before entering the lumen 40' through the side openings. Where a sheath 50' is used, the secondary guidewire 22 is also inserted into the side opening (not shown) of the sheath, as described above with respect to the first embodiment.

The primary balloon catheter assembly is then advanced along the guidewires 20 and 22 in the primary vessel 14 until the distal end reaches the bifurcation area 18. At that point, as described above with respect to the transition from FIGS. 2 and 4, where the primary guidewire 20 and the secondary guidewire 22 diverge, the secondary guidewire 22 is released from the peel-away wire guide 44' such that the side openings 30', 42' and 72 are in alignment with the secondary vessel 16.

The primary balloon stent 24' is then deployed by expanding the stent with pressure from the expanding balloon 70 provided by an appropriate fluid, such as saline solution, such that the primary balloon stent 24' would have the position shown for the self-expandable stent 24 depicted in FIG. 5, to maintain the patency of the primary vessel 14. Thereafter, the primary stent catheter 38', the balloon 70 and the primary guidewire 20 all may be withdrawn from the primary vessel 14. This leaves the arrangement as shown in FIG. 5 where the primary stent 24' has been expanded and deployed and the secondary guidewire 22 remains in the secondary vessel 16 and the primary vessel 14.

A secondary balloon stent (not shown) is then mounted around a secondary balloon (not shown), which in turn is mounted on a secondary stent catheter (not shown). All of these components, while not shown in the drawings, all are similar to the arrangement shown in FIG. 6 for the self-expandable catheter, stent and sheath assembly. Since a balloon catheter is being used, a secondary sheath is not required, but is also optional. The secondary guidewire 22 is then threaded into a lumen in the secondary catheter and the catheter and stent assembly are moved along the secondary guidewire through the side opening 30 in the expanded primary stent 24 or 24' into the bifurcation area 18 and also into the secondary vessel 16 for appropriate expansion as described above with respect to FIGS. 7 and 8, but using the balloon expansion technique described above with respect to FIG. 9. The resulting expanded balloon secondary stent 24' would then be installed in the secondary vessel 16 to maintain the patency of the secondary vessel 16 in communication with the primary stent as shown in FIG. 8.

The method of the present invention for placing a stent assembly in a bifurcated vessel in an animal body is efficient and elegant, allowing for positive placement without overcrowding stents and catheters with excess balloons and other components. By threading the primary stent assembly, including any catheter, balloon or sheath used therewith along both guidewires, and allowing for the release of the secondary guidewire 22 from the distal end of the primary catheter and stent assembly, efficient and appropriate placement of the primary stent in the bifurcation area 18 is accomplished readily. By removing the primary catheter assembly and any associated sheaths or balloons after the expansion of the primary stent, along with the removal of the primary guidewire 20, the primary vessel is relieved of that apparatus. Yet by retaining the secondary guidewire 22 in position within the primary vessel 14 and the secondary vessel 16, easy, efficient and positive location and alignment of the secondary stent 32 within the secondary vessel 16 is accomplished readily by advancing the secondary stent and catheter assembly along the secondary guidewire into position passed the bifurcation area 18 and into the secondary vessel 16. This allows for the complete support of the bifurcated vessel 12 by the primary stent 24 and secondary stent 32, as shown in FIG. 8.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for placing a stent assembly in a bifurcated vessel in an animal body, the method comprising:
    (a) locating and assessing an area in the body for placement of a stent assembly in a primary vessel and a secondary vessel at a location where the primary vessel and the secondary vessel intersect at a bifurcation area;

(b) inserting a primary guidewire from a location external of the body through the primary vessel beyond the bifurcation area;

(c) inserting a secondary guidewire from a location external of the body through the primary vessel and into the secondary vessel, a distal portion of the secondary guidewire being retained in place within the secondary vessel until after placement of a primary stent in the primary vessel and a secondary stent in the secondary vessel;

(d) selecting a primary stent having a lumen, a side opening, a proximal end region and a distal end region, the primary stent being configured to fit within the primary vessel in the bifurcation area, and when expanded, to maintain patency of the primary vessel where the primary stent is installed;

(e) mounting the primary stent on a primary stent catheter having a body including a lumen extending through the primary stent catheter to a distal end of the primary stent catheter, the primary stent catheter having a side opening in the body proximal to the distal end of the primary stent catheter, the mounting of the primary stent being such that the primary stent is expandable when in position in the bifurcation area, and such that the side opening of the primary stent is aligned with the side opening of the primary stent catheter;

(f) inserting the primary guidewire through the lumen of the primary stent catheter surrounded by the distal end portion of the primary stent and extending through the lumen of the primary stent catheter surrounded by the proximal end region of the primary stent;

(g) inserting the secondary guidewire into the side openings of the primary stent and the primary stent catheter and extending through the lumen of the primary stent catheter surrounded by the proximal end region of the primary stent;

(h) after (b) and (c), passing the primary stent catheter through the primary vessel and into the bifurcated area for placement of the primary stent within the primary vessel;

(i) expanding the primary stent to maintain patency of the primary vessel in and adjacent to the bifurcation area, such that the side opening in the primary stent is aligned with the secondary vessel;

(j) withdrawing the primary stent catheter and the primary guidewire from the primary vessel, while retaining the secondary guidewire in the primary and secondary vessels;

(k) selecting a secondary stent having a lumen, a proximal end region and a distal end region, the secondary stent being configured to fit within the secondary vessel in the bifurcation area, and when expanded, to maintain patency of the secondary vessel where the secondary stent is installed;

(l) mounting the secondary stent on a secondary stent catheter having a lumen such that the secondary stent is expandable when in position through the side opening of the primary stent in the bifurcation area and when in position in the secondary vessel;

(m) inserting the secondary guidewire into the secondary stent catheter lumen beginning from a portion surrounded by the distal end region of the secondary stent and extending through the lumen of the secondary stent catheter surrounded by the proximal end region of the secondary stent;

(n) after (c), passing the secondary stent catheter along the secondary guidewire through the primary vessel, through the proximal end region and side opening of the expanded primary stent into the bifurcated area for placement of the secondary stent within the secondary vessel and in fluid communication with the expanded primary stent;

(o) expanding the secondary stent to maintain patency of the secondary vessel such that the proximal end region of the secondary stent is in fluid communication and in contact with the side opening of the expanded primary stent; and (p) withdrawing the secondary stent catheter and the secondary guidewire from the secondary and primary vessels to a location external of the body.

2. The method of claim 1, wherein a peel-away wire guide having a releasable longitudinal closure member is mounted on a portion of the primary stent catheter distal of the distal end region of the primary stent when the primary stent is mounted on the primary stent catheter, and wherein the method further comprises inserting the secondary guidewire into the peel-away wire guide and thereafter into the aligned side openings of the primary stent and the primary stent catheter, the peel-away wire guide being adapted to retain the secondary guidewire therein until the primary stent catheter moves within the primary vessel to a point where the primary guidewire and secondary guidewire diverge and the secondary guidewire overcomes friction forces of the releasable longitudinal closure member, thereby longitudinally releasing the secondary guidewire from the peel-away wire guide through a side of the releasable longitudinal closure member.

3. The method of claim 1, wherein the animal is a human.

4. The method of claim 3, wherein the bifurcated vessel is a vascular vessel.

5. The method of claim 4, wherein the vascular vessel is a coronary vessel.

6. The method of claim 1, wherein the primary stent is self-expandable, and wherein (e) of the method further comprises mounting the primary stent on the primary stent catheter and surrounding the mounted primary stent with a primary stent sheath having a primary stent sheath side opening aligned with the side openings of the primary stent catheter and the primary stent, and having a longitudinal groove extending between the primary stent sheath side opening and a distal end of the primary stent sheath, whereby when the distal end of the primary stent sheath reaches a point of divergence of the primary guidewire and the secondary guidewire as the primary stent catheter passes through the primary vessel, the secondary guidewire passes through the groove to the aligned side openings in the primary stent catheter, the primary stent and the primary stent sheath, and where (i) further comprises withdrawing the primary stent sheath to allow the primary stent to expand when in position in the bifurcation area.

7. The method of claim 6, wherein the secondary stent is self-expandable, and wherein (l) further comprises mounting the secondary stent on the secondary stent catheter and surrounding the mounted secondary stent with a secondary stent sheath, and wherein (o) further comprises withdrawing the secondary stent sheath to allow the secondary stent to expand when the secondary stent is in position within the secondary vessel.

8. The method of claim 1, wherein the primary stent is a balloon-expandable stent, and wherein (e) further comprises mounting the primary stent around a primary balloon which in turn is mounted on the primary stent catheter, the primary balloon having a primary balloon side opening in alignment with the primary stent catheter side opening and the primary stent side opening, and wherein (i) further comprises expanding the primary balloon to expand the primary stent.

9. The method of claim 8, wherein the secondary stent is a balloon-expandable stent and wherein (l) further comprises mounting the secondary stent around a secondary balloon which in turn is mounted on the secondary stent catheter, and wherein (o) further comprises expanding the secondary balloon to expand the secondary stent.

10. The method of claim 1, wherein the secondary stent is inserted through the side opening of the primary stent, such that the secondary stent forms an angle of about 20° to about 120° with respect to the primary stent.

11. The method of claim 10, wherein the angle is about 30°.

12. The method of claim 10, wherein the angle is about 45°.

13. The method of claim 10, wherein the angle is about 90°.

14. The method of claim 1, wherein the primary stent has an expanded diameter of about 2 mm to about 50 mm, and the secondary stent has an expanded diameter of about 2 mm to about 15 mm.

15. The method of claim 14, wherein the primary stent has an expanded diameter of about 20 mm to about 50 mm, and the secondary stent has a diameter selected from the group consisting of about 2 mm to about 6 mm, about 4 mm to about 10 mm and about 8 mm to about 15 mm.

16. The method of claim 1, wherein the primary stent has an expanded length of about 10 mm to about 40 mm.

17. The method of claim 1, wherein the secondary stent has an expanded length of about 15 mm to about 40 mm.

* * * * *